(12) United States Patent
Bristow

(10) Patent No.: US 10,499,643 B2
(45) Date of Patent: Dec. 10, 2019

(54) SYNERGISTIC HERBICIDAL COMPOSITION AND THE METHOD OF CONTROLLING THE GROWTH OF UNDESIRED PLANTS

(71) Applicant: JIANGSU ROTAM CHEMISTRY CO., LTD, Jiangsu (CN)

(72) Inventor: James Timothy Bristow, Chai Wan (HK)

(73) Assignee: JIANGSU ROTAM CHEMISTRY CO., LTD, Jiangsu (CN)

( * ) Notice: Subject to any disclaimer, the term of this patent is extended or adjusted under 35 U.S.C. 154(b) by 0 days.

(21) Appl. No.: 16/065,683

(22) PCT Filed: Feb. 3, 2017

(86) PCT No.: PCT/CN2017/072843
§ 371 (c)(1),
(2) Date: Jun. 22, 2018

(87) PCT Pub. No.: WO2017/129143
PCT Pub. Date: Aug. 3, 2017

(65) Prior Publication Data
US 2019/0000083 A1    Jan. 3, 2019

(30) Foreign Application Priority Data
Jan. 29, 2016 (AU) ................. 2016200567

(51) Int. Cl.
*A01N 43/80* (2006.01)
*A01N 47/36* (2006.01)

(52) U.S. Cl.
CPC ............. *A01N 43/80* (2013.01); *A01N 47/36* (2013.01)

(58) Field of Classification Search
None
See application file for complete search history.

(56) References Cited

U.S. PATENT DOCUMENTS

2011/0015067 A1    1/2011 Sievernich et al.

FOREIGN PATENT DOCUMENTS

| AU | 2016200567 B1 | 1/2017 |
| CN | 102065692 A | 5/2011 |
| WO | 2012176938 A1 | 12/2012 |

OTHER PUBLICATIONS

Australian First Examination Report regarding Application No. AU2016200567 dated Sep. 30, 2016.
Hardwick, Jon Marshall, B.S., Louisiana State University, 2011, Dec. 2013: Evaluation of Pyroxasulfone in Corn (*Zea mays* L.) and Soybean (*Glycine max* L. Merr.) Weed Management Programs; A Thesis Submitted to the Graduate Faculty of the Louisiana State University and Agricultural and Mechanical College in partial fulfillment of the requirements for the degree of Master of Science in the School of Plant, Environmental, and Soil Sciences.
International Search Report and Written Opinion regarding Application No. PCT/CN2017/072843 dated May 9, 2017.
European Search Report corresponding to European Application No. EP 17 74 3758 dated May 21, 2019.

*Primary Examiner* — Alton N Pryor
(74) *Attorney, Agent, or Firm* — Dickinson Wright PLLC

(57) ABSTRACT

A synergistic herbicidal composition comprising Pyroxasulfone and Thifensulfuron methyl as the active components, as well as the use of the synergistic herbicidal composition for controlling the growth of undesirable plants is provided. A method of controlling the growth of undesirable plants, which comprises applying the active components Pyroxasulfone and Thifensulfuron methyl of the synergistic herbicidal composition to the undesirable plants or their growing locus jointly or separately is also provided. A method of reducing or preventing harm caused by Pyroxasulfone when applied to plants, seeds or other reproductive parts of useful crops is also provided.

13 Claims, No Drawings

SYNERGISTIC HERBICIDAL COMPOSITION AND THE METHOD OF CONTROLLING THE GROWTH OF UNDESIRED PLANTS

CROSS REFERENCE TO RELATED APPLICATIONS

This application is a 371 national phase entry of PCT/CN2017/072843 filed on 3 Feb. 2017, which claims priority benefit of AU Patent Application No. AU2016200567 filed Jan. 29, 2016, the contents of which are incorporated herein by reference in their entirety.

FIELD

The present invention relates to a synergistic herbicidal composition and a method of controlling the growth of undesirable plants.

BACKGROUND

The yield of agriculture crops may be reduced as a result of the hazard of weeds. In order to retrieve the loss of yield, a large amount of herbicides have to be applied to control the weeds each year. In recent year, agricultural crops confront increasing hazard from weeds. Moreover, the abuse of herbicides has increased the resistance of weeds against pesticides, leading to declined efficacy of weeds control year by year.

The traditional method of enhancing herbicidal activity and broadening herbicidal spectrum of existing herbicides is to mix two or more herbicidal substances with different herbicidal activity. If mix two or more herbicidal active chemicals, its herbicidal efficacy may be more prominent than applying a single herbicide. When the efficacy of a mixture with two or more ingredients exceeds the anticipated efficacy of each ingredient, it is called "synergistic effects". However, only under certain circumstances, when two or more substances having herbicidal activity are mixed together, the herbicidal mixture exhibits synergistic effects. As a result of the difference in herbicidal efficacy, absorption rate, transmission and metabolism and so on, the herbicidal activity of most mixtures is lower than that of each ingredient when applied separately. The "Antagonistic Effects" has described such situation that when the efficacy of a mixture with two or more ingredients having herbicidal activity is lower than the anticipated efficacy of each ingredient when applied separately. The "Additive Effect" has described such situation that the herbicidal efficacy of mixture of two or more substances having herbicidal activity equals to the herbicidal efficacy of each ingredients applied separately.

Pyroxasulfone, with chemical name as 3-[5-(difluoromethoxy)-1-methyl-3-(trifluoromethyl) pyrazol-4-ylmethylsulfonyl]-4,5-dihydro-5,5-dimethyl-1,2-oxazole, is represented by the following chemical structure:

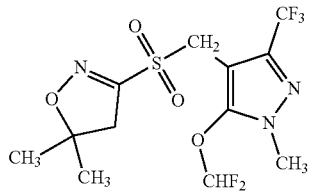 [SMILES: Cn1nc(C(F)(F)F)c(CS(=O)(=O)C2=NOC(C)(C)C2)c1OC(F)F]

Pyroxasulfone was described in EP1364946 and US20050256004. Although Pyroxasulfone is a highly effective pre-emergence herbicide, its activity becomes low after the emergence. When Pyroxasulfone is applied to certain dicotyledonous crops, such as cotton, sunflower, soybean, and brassica crops, such as canola and oil rape and some gramineous crops, such as rice, wheat, rye and barley, the crops may suffer from unacceptable level of harms.

Thifensulfuron methyl, also named "Londax", is represented by the following structure:

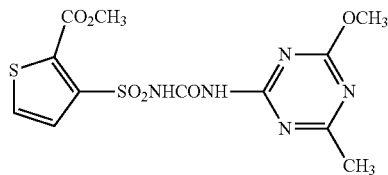

Thifensulfuron methyl is systemic conductive post-emergence selective herbicides, and an inhibitor of branched-chain amino acid synthesis, which is capable of inhibiting the biosynthesis of valine, leucine and isoleucine to prevent cell division, then stop sensitive crops from growing. It is mainly applied to control broadleaves weeds in the field of wheat, barley, oats, corn, such as redroot pigweed, purslane, descurainia sophia, capsella, salsola, catchweed bedstraw, speedwell and Malachium aquaticum (L.), while it is ineffective to thistle, bindweed and grass weeds. In general, the sensitive weeds stop growing after application and die after 1 week.

In the current, the herbicide spectrum is limited because of regulation to ensure the safety of crops. Application of a single herbicide is unable to completely and effectively control the weeds in the field of crops, on the other side, over-dosed herbicide or unevenly application is likely to produce unacceptable toxic to current crops or post-harvest crops. Pyroxasulfone is a highly effective herbicide used before emergence, but becomes less active after the emergence stage. Besides, the compatibility of Pyroxasulfone with some dicotyledonous crops, such as cotton, sunflower and beans, brassica crops, such as canola and oil rape, and certain gramineous crops, such as rice, wheat, rye and barley, is not ideal, as it not only damages the target plants, but also harms crops at unacceptable level. In principle, the damage to crops can be eased by decreasing the application rate, while its efficacy of control target plants also reduced accordingly.

SUMMARY

It is surprising to find that, the synergistic herbicidal composition of Pyroxasulfone and Thifensulfuron methyl has achieved synergistic effect in controlling the growth of undesirable plant, which significantly reduces the amount of active components to control weeds, as well as mitigates or prevents the harms on plants, seeds or other reproductive parts of useful crops after been treated by Pyroxasulfone. The herbicidal activity of the composition of Pyroxasulfone and Thifensulfuron methyl is greater than the sum activity of individual compound.

In one aspect, the present invention provides a synergistic herbicidal composition, which is not only able to enhance the efficacy of weed control, but also improve the safety of crops, reduce the herbicide application cost and extend the applicable scope. The synergistic herbicidal composition comprises the active components Pyroxasulfone and Thifensulfuron methyl, wherein the weight ratio of active components Pyroxasulfone and Thifensulfuron methyl ranges from 50:1 to 1:50, preferably from 25:1 to 1:25, more preferably from 10:1 to 10:1, and still more preferably from 5:1 to 1:5.

The synergistic herbicidal composition may comprise active components Pyroxasulfone, Thifensulfuron methyl, surfactant and/or filler.

The active components Pyroxasulfone and Thifensulfuron methyl are present in the said synergistic herbicidal composition in an amount of 5%-90% by weight, 10%-80% by weight or 20%-60% by weight.

The synergistic herbicidal composition may be provided as a formulation selected from a Wettable Powder (WP), an Emulsifiable Concentrate (EC), a Suspension Concentrate (SC), a Capsule Suspension (CS), a Micro-emulsion (ME), an Oil-in-water Emulsion (EW), Suspo-emulsion (SE), Water Dispersible Granules (WDG), an Aqueous Solution (AS), a Capsule Suspension (CS) and an Ultra-low Volume Liquid (ULV).

The present invention provides a use of the synergistic herbicidal composition in controlling undesirable plants.

More particularly, the use of the synergistic herbicidal composition in controlling the growth of undesirable plants, including broadleaf weeds, sedges and gramineous weeds.

The present invention also relates to a use of the synergistic herbicidal composition in controlling the growth of undesirable plants within useful crops, especially useful crops that are resistant to said synergistic herbicidal composition such as wheat, barley, rye, triticale, hard wheat, rice, corn, sugar cane, sorghum, soy bean, peas, beans, lentils, peanut, sun flower, sugar beet, potato, cotton, oil rape, canola, leaf mustard, cabbage, turnip, turf, grapes, peach, almond, walnut, olive, cherry, plum, apricot, citrus and pistachio.

In a further aspect, the present invention provides a method of controlling the growth of undesirable plants, comprising applying a herbicidal effective amount of the synergistic herbicidal composition of the present invention to the undesirable plants or their locus of growth (i) before germination of the undesirable plant (pre-emergence); (ii) after germination of the undesirable plant (post-emergence), or (iii) (i) and (ii).

In the method of controlling the growth of undesirable plants, the active components Pyroxasulfone and Thifensulfuron methyl of synergistic herbicidal composition of the present invention may be applied to the undesirable plants or their growing locus jointly or separately.

Further, the method to control the growth of undesirable plants may include the application of the synergistic herbicidal composition of the present invention in the presence of the plants, seeds or other reproductive parts of useful crops.

A method to reduce or prevent the harms from Pyroxasulfone when it's treated on the plants, seeds or other reproductive parts of useful crops, including the application of the synergistic herbicidal composition of the present invention to treat the plants, seeds or other reproductive parts of the useful crops.

The efficacy of the synergistic herbicidal composition of the present invention is more effective than each active ingredient when they are applied separately and the present invention is characterized by delaying the weeds to form drug-resistance, having wider herbicide spectrum, long period of effect and capable of controlling annual gramineous weeds, broadleaf weeds and sedge weeds in the field, as well as being safe to the useful crops and the post-harvest crops.

DETAILED DESCRIPTION OF EXAMPLE EMBODIMENTS

The synergistic efficacy is able to reduce the application rate of single herbicide, increase its efficacy at the same application rate, control the variety that is never been protected before, control the varieties having tolerance or resistance to single or several herbicides, prolong the application period and/or reduce the times of a single application. It provides the user a weed control system that is more economical and ecological.

One aspect of the present invention provides a synergistic herbicidal composition comprising active components Pyroxasulfone and Thifensulfuron methyl, wherein the weight ratio of active components Pyroxasulfone and Thifensulfuron methyl ranges from 50:1 to 1:50, preferably from 25:1 to 1:25, more preferably from 10:1 to 1:10, still more preferably from 5:1 to 1:5.

The synergistic herbicidal composition of embodiments of the present invention is able to synergize the activity of active components Pyroxasulfone and Thifensulfuron methyl in an unprecedented manner, which exceeds the combined activities when each active component, Pyroxasulfone and Thifensulfuron methyl, is applied separately.

The present invention also provides a synergistic herbicidal composition, comprising Pyroxasulfone and Thifensulfuron methyl, and filler and/or surfactants.

If use water as filler, other secondary solvent can be added, such as organic solvent. The main suitable liquid solvents are selected from aromatic compound, including xylene, toluene or alkyl naphthalene; chlorinated aromatic hydrocarbons and chlorinated aliphatic hydrocarbons, such as chlorobenzene, vinyl chloride or dichloromethane; aliphatic hydrocarbons, for example cyclohexane or paraffin, such as mineral oil fraction, mineral oil and plant oil; alcohols, such as butanol or ethylene glycol and its ethers and esters; ketones, such as acetone, methyl ethyl ketone, methyl isobutyl ketone or cyclohexanone; strong polar solvents, such as dimethylformamide and dimethyl sulfoxide, and water.

If the filler is solid, the suitable carrier are selected from ammonium salt; grinded nature minerals, such as kaolin, clay, talc, chalk, quartz, attapulgite, montmorillonite or diatomite; grinded synthetic mineral, such as highly dispersed silica, alumina and silicate; grinded and graded natural minerals, such as calcite, marble, pumice, sepiolite and dolomite; inorganic and organic synthesized particles; organic materials (for example saw dust, coconut shell and corn).

The suitable surfactants are selected from nonionic and anionic emulsifier, for example polyethoxylated fatty acid ester, polyethoxylated fatty alcohol ether, such as alkylaryl polyethyleneglycol ether, alkyl sulfonate, alkyl sulfate, aryl sulfonate and protein hydrolysate; the suitable dispersing agents are selected from sulfite lignin and methylcellulose.

The suitable colorants can be selected from inorganic pigment, such as ironoxide, titania and prussian blue; and organic pigment, such as alizarin colorant, azo colorant and metal phthalocyanine colorant.

The suitable tackifier can be selected from carboxymethyl cellulose; natural and synthetic polymer in the form of powder, granules or latex, such as arabic gum, polyvinyl alcohol and polyvinyl acetate; and natural phospholipid, such as cephalin and lecithin, and synthetic lipid. Other additives might be mineral oil and plant oil.

The suitable micronutrients can be selected from iron salt, manganese salt, boron salt, copper salt, cobalt salt, molybdenum salt and zinc salt.

The active components Pyroxasulfone and Thifensulfuron methyl are present in aforesaid synergistic herbicidal composition in an amount of from 5%-90%, preferably from 10%-80%, more preferably from 20%-60%.

The synergistic herbicidal composition of the present invention is particularly advantageous as the said active components Pyroxasulfone and Thifensulfuron methyl have been added in an optimum proportion. Moreover, the filler and/or surfactants in the formulation can be adjusted with each other.

The synergistic herbicidal composition of the present invention can be prepared in any traditional formulation. The examples of foliar application formula of premix composition include:

GR: a granule
WP: a wettable powder
WG: a water-dispersible granule
SG: a water-soluble granule
SL: a water-soluble concentrate
EC: an emulstifiable concentrate
EW: an emulsion, oil-in-water
ME: a micro-emulsion
SC: a suspension concentrate
CS: a microencapsulated suspension
OD: an oil-based suspension concentrate
SE: an aqueous suspo-emulsion
FS: a flowable concentrate for seed treatment
ULV: an ultra-low volume liquid In embodiments of the present invention, it is prepared to choose Wettable Powder (WP), Emulsifiable Concentrate (EC), Suspension Concentrate (SC), Micro-capsule (MC), Micro-emulsion (ME), Oil-in-water Emulsion (EW), Aqueous Suspo-emulsion (SE), Water-dispersible Granule (WG), Water-soluble Granule (SG), Aqueous Solution (AS), Microencapsulated Suspension (CS) and Ultra-low Volume Liquid (ULV). All of above formulations are conventional in the art and their preparation methods are well known to those skilled the art.

The formulations which are suitable for tank-mixed composition include solution, diluted emulsion, suspension or their mixture and powder. Normally, the tank-mixed composition refers to a premix composition which comprises different pesticides and one or more further optional adjuvant after dilution by solvent (e.g. water).

The synergistic herbicidal composition can also be mixed with other known active compounds, such as herbicides, fungicides, insecticides, acaricides, nematicides, safeners, bird repellents, plant nutrients and soil structure modifiers.

Preferably, the synergistic herbicidal composition of the present invention still can comprise other herbicides known in the art. The other known herbicides or plant growth regulators suitable to be combined with the active compounds of the present invention are for example the following active compounds (which refers to the compounds that are named according to ISO or chemical or code names), as well as include the applicable forms thereof, such as acid, salt, ester and isomers, such as stereoisomer and optical isomer, for example acetochlor, acibenzolar, acibenzolar-S-methyl, acifluorfen, acifluorfen-sodium, aclonifen, alachlor, allidochlor, alloxydim, alloxydim-sodium, ametryn, amicarbazone, amidosulfuron, aminocyclopyrachlor, aminopyralid, amitrole, ammonium sulfamate, ancymidol, anilofos, asulam, atrazine, azafenidin, azimsulfuron, aziprotryn, beflubutamid, benazolin, benazolin-ethyl, bencarbazone, benfluralin, benfuresate, bensulide, bentazone, benzfendizone, benzobicyclon, benzofenap, benzofluor, benzoylprop, bicyclopyrone, bifenox, bilanafos, bilanafos-sodium, bispyribac, bispyribac-sodium, bromacil, bromobutide, bromofenoxim, bromoxynil, bromuron, buminafos, busoxinone, butachlor, butafenacil, butamifos, butenachlor, butralin, butroxydim, butylate, cafenstrole, carbetamide, carfentrazone, carfentrazone-ethyl, chlomethoxyfen, chloramben, chlorazifop, chlorazifop-butyl, chlorbromuron, chlorbufam, chlorfenac, chlorfenac-sodium, chlorfenprop, chlorflurenol, chlorflurenol-methy, chloridazon, chlorimuron, chlorimuron-ethyl, chlormequat chloride, chlornitrofen, chlorophthalim, chlorthal-dimethyl, chlorotoluron, chlorsulfuron, cinidon, cinidon-ethyl, cinmethylin, cinosulfuron, clethodim, clodinafop, clodinafop-propargyl, clofencet, clomazone, clomeprop, cloprop, clopyralid, cloransulam, cloransulam-methyl, cumyluron, cyanamide, cyanazine, cyclanilide, cycloate, cyclosulfamuron, cycloxydim, cycluron, cyhalofop, cyhalofop-butyl, cyperquat, cyprazine, cyprazole, 2,4-D, 2,4-DB, daimuron/dymron, dalapon, daminozide, dazomet, n-decanol, desmedipham, desmetryn, detosyl-pyrazolate (DTP), diallate, dichlobenil, 2,4-dichlorprop, 2,4-dichlorprop-P, diclofop, diclofop-methyl, diclofop-P-methyl, diclosulam, diethatyl, diethatyl-ethyl, difenoxuron, difenzoquat, diflufenican, diflufenzopyr, diflufenzopyr-sodium, dikegulac-sodium, dimefuron, dimepiperate, dimethachlor, dimethametryn, dimethenamid, dimethenamid-P, dimethipin, dimetrasulfuron, dinitramine, dinoseb, dinoterb, diphenamid, dipropetryn, diquat, diquat dibromide, dithiopyr, diuron, eglinazine-ethyl, endothal, esprocarb, ethalfluralin, ethametsulfuron, ethametsulfuron-methyl, ethephon, ethidimuron, ethiozin, ethofumesate, ethoxyfen, ethoxyfen-ethyl, ethoxysulfuron, etobenzanid, F-5331 (N-[2-chloro-4-fluoro-5-[4-(3-fluoropropyl)-4,5-dihydro-5-oxo-1H-tetrazol-1-yl]phenyl]ethylsulfonamide), F-7967 (3-[7-chloro-5-fluoro-2-(trifluoromethyl)-1H-benzoimidazol-4-yl]-1-methyl-6-(trifluoromethyl)pyrimidine-2,4(1H, 3H)-dione, 2,4,5-fenoprop, fenoxaprop, fenoxaprop-P, fenoxaprop-ethyl, fenoxaprop-P-ethyl, fentrazamide, fenuron, flamprop-M-isopropyl, flamprop-M-methyl, flazasulfuron, florasulam, fluazifop, fluazifop-P, fluazifop-butyl, fluazifop-P-butyl, fluazolate, flucarbazone, flucarbazone-sodium, flucetosulfuron, fluchloralin, flufenacet (thiafluamide), flufenpyr, flufenpyr-ethyl, flumetralin, flumetsulam, flumiclorac, flumiclorac-pentyl, flumioxazin, flumipropyn, fluometuron, fluorodifen, fluoroglycofen, fluoroglycofen-ethyl, flupoxam, flupropacil, flupropanate, flupyrsulfuron, flupyrsulfuron-methyl-sodium, flurenol, flurenol-butyl, fluridone, flurochloridone, fluroxypyr, fluroxypyr-meptyl, flurprimidol, flurtamone, fluthiacet, fluthiacet-methyl, fluthiamide, fomesafen, foramsulfuron, forchlorfenuron, fosamine, furyloxyfen, gibberellic acid, glufosinate, glufosinate-ammonium, glufosinate-P, glufosinate-P-ammonium, glufosinate-P-sodium, glyphosate, glyphosate-isopropylammonium, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HW-02 (1-(dimethoxyphosphoryl)ethyl (2,4-dichlorophenoxy)acetate), imazamethabenz, imazamethabenz-methyl, imazamox, imazamox-ammonium, imazapic, imazapyr, imazapyr-isopropylammonium, imazaquin, imazaquin-ammonium, imazethapyr, imazethapyr-ammonium, imazosulfuron, inabenfide, indanofan, indaziflam, indole acetic acid (IAA), 4-indol-3-yl butyric acid (IBA), iodosulfuron, iodosulfuron-methyl-sodium, ioxynil, ipfencarbazone, isocarbamid, isopropalin, isoproturon, isouron, isoxaben, isoxachlortole, isoxaflutole, isoxapyrifop, KUH-043 (3-({[5-(difluoromethyl)-1-methyl-3-(trifluoromethyl)-1H-pyrazol-4-yl]methyl}sulfonyl)-5,5-dimethyl-4,5-dihydro-1,2-oxazole), karbutilate, ketospiradox, lactofen, lenacil, linuron, maleic hydrazide, 2-methyl-4-chlorophenoxyacetic acid (MCPA), 2-methyl-4-chlorophenoxybutyric acid (MCPB), methyl 2-methyl-4-chlorophenoxybutyrate (MCPB-methyl), ethyl 2-methyl-4-chlorophenoxybutyrate (MCPB-ethyl), Z-[(4-chloro-o-phenyl)oxy]propionic acid (mecoprop), Z-[(4-chloro-o-phenyl)oxy]propionic acid sodium (mecoprop-sodium), mecoprop-butotyl, mecoprop-P-butotyl, P—Z-[(4-chloro-o-phenyl)oxy]propionic acid dimethyl ammonium (mecoprop-P-dimethylammonium), P—Z-[(4-chloro-o-phenyl)oxy]propionic acid ethylhexyl ester (mecoprop-P-2-ethylhexyl), P—Z-[(4-chloro-o-phenyl)oxy]propionic acid potassium, mefluidide, mepiquat-chloride, mesosulfuron, mesosulfuron-methyl, mesotrione, methabenzthiazuron, metam, metamifop, metamitron, metazachlor, metazasulfuron, methazole, methiopyrsulfuron, methiozolin, methoxyphenone, methyldymron, 1-methylcyclopropene, methyl isothiocyanate, metobenzuron, metobromuron, metolachlor, S-metolachlor, metosulam, metoxuron, metsulfuron, molinate, monalide, monocarbamide dihydrogensulfate, monolinuron, monosulfuron, monosulfuron ester, monuron, MT128 (6-chloro-N-[(2E)-3-chloropropy-2-ene-1-yl]-5-methyl-N-phenylpyridazine-3-amine), naproanilide, napropamide, naptalam, neburon, nicosulfuron, nipyraclofen, nitralin, nitrofen, nitrophenol sodium (mixture of isomers), nitrofluorfen, nonanoic acid, norflurazon, orbencarb, orthosulfamuron, oryzalin, oxadiargyl, oxadiazon, oxasulfuron, oxaziclomefone, oxyfluorfen, paclobutrazol, paraquat, paraquat dichloride, pelargonic acid, nonanoic acid, pendimethalin, pendralin, penoxsulam, pentanochlor, pentoxazone, perfluidone, pethoxamid, phenisopham, phenmedipham, phenmedipham-ethyl, picloram, picolinafen, pinoxaden, piperophos, pirifenop, pirifenop-butyl, pretilachlor, primisulfuron, primisulfuron-methyl, probenazole, profluazo, procyazine, prodiamine, prifluraline, profoxydim, prohexadione, prohexadione-calcium, prohydrojasmone, prometon, propachlor, propanil, propaquizafop, propazine, propham, propisochlor, propoxycarbazone, propoxycarbazone-sodium, propyrisulfuron, propyzamide, prosulfalin, prosulfocarb, prosulfuron, prynachlor, pyraclonil, pyraflufen, pyraflufen-ethyl, pyrasulfotole, pyrazolynate, pyrazolate, pyrazosulfuron, pyrazosulfuron-ethyl, pyrazoxyfen, pyribambenz, pyribambenz-isopropyl, pyribambenz-propyl, pyributicarb, pyridate, pyriftalid, pyriminobac, pyriminobac-methyl, pyrimisulfan, pyrithiobac, pyrithiobac-sodium, pyroxsulam, quinchlorac, quinmerac, quinoclamine, quizalofop, quizalofop-ethyl, quizalofop-P, quizalofop-P-ethyl, quizalofop-P-tefuryl, rimsulfuron, saflufenacil, secbumeton, sethoxydim, siduron, simazine, simetryn, sulcotrione, sulfallate, CDEC, sulfentrazone, sulfometuron, sulfometuron-methyl, sulfosate(glyphosate-trimesium), sulfosulfuron, SYN-523, tebutam, tebuthiuron, tecnazene, tefuryltrione, tembotrione, tepraloxydim, terbacil, terbucarb, terbuchlor, terbumeton, terbuthylazine, terbutryn, thenylchlor, thiafluamide, thiazafluron, thiazopyr, thidiazimin, thidiazuron, thiencarbazone, thiencarbazone-methyl, bensulfuron-methyl, thiobencarb, tiocarbazil, topramezone, tralkoxydim, triallate, triasulfuron, triaziflam, triazofenamide, tribenuron-methyl, trichloroacetic acid (TCA), triclopyr, tridiphane, trietazine, trifloxysulfuron, trifloxysulfuron-sodium, trifluralin, triflusulfuron, triflusulfuron-methyl, trimeturon, trinexapac, trinexapac-ethyl, tritosulfuron, tsitodef, uniconazole, uniconazole-P, vernolate and other compounds.

The synergistic herbicidal composition of the present invention may also comprise one or more safeners. Safener refers to an organic compound which can lead to better compatibility among crops when applied under certain condition with specifically effective herbicides jointly. Safener usually plays the role as antidote or antagonist in the crops in order to reduce or even prevent harms from crops.

The application of above safener at antidotally effective amount is able to reduce the phytotoxicity and side effect of herbicides, such as those used on economically important crops or fruit plantation (plantation crops). The aforesaid economically important crops include cereals (wheat, barley, rye, oat, corn, rice, millet), sugar beet, sunflower, sugarcane, oil rape, cotton and soybeans.

Following are the compounds suitable to be used as safeners (including possible stereoisomer and ester or salt commonly used for agriculture): benoxacor, cloquintocet(-mexyl), cyometrinil, cloquintocet, cyometrinil, cyprosulfamide, dichlormid, dicyclonon, o-phenyl phosphorothionate o, o-dietholate, fenchlorazole(-ethyl), fenclorim, flurazole, fluxofenim, furilazole, mefenpyr, isoxadifen(-ethyl), mefenpyr(-diethyl), mephenate, naphthalic anhydride, oxabetrinil), 2,2,5-trimethyl-3-(dichloroacetyl)-1,3-oxazolidine, 4-(dichloroacetyl)-1-oxa-4-aza-spiro[4,5]decane and agriculturally acceptable salt and their agriculturally acceptable derivatives when they have carboxyl group. The preferable safeners used in the synergistic herbicidal composition of the present invention can be selected from benoxacor, cloquintocet, cyprosulfamide, dichlormid, fenchlorazole(-ethyl), fenclorim, fluxofenim, furilazole, mefenpyr, naphthalic anhydride, 2,2,5-trimethyl-3-(dichloroacetyl)-1,3-oxazolidine and 4-(dichloroacetyl)-1-oxa-4-aza-spiro[4,5]decane.

The weight ratio between the synergistic herbicidal composition of the present invention and safener will vary widely according to the application rate of herbicides and the efficacy of said safeners, such as ranges from 90000:1 to 1:5000, preferably from 7000:1 to 1:1600, in particular from 3000:1 to 1:500. The safener can be prepared with active components Pyroxasulfone and Thifensulfuron methyl in the form of finished formulation or provided and applied as tank mixture with said herbicidal composition.

The present invention has also provided a use of a synergistic herbicidal composition in controlling the growth of undesirable plants.

More particularly, the use of a synergistic herbicidal composition in controlling the growth of undesirable plants, including broadleaf weeds, sedge weeds and gramineous weeds.

The synergistic herbicidal composition of the present invention has good herbicidal activity particularly effective to a wide spectrum of economically important undesirable plants, either monocotyledonous weeds or dicotyledonous weeds, such as broadleaf weeds, sedge weeds or gramineous weeds, including those tolerant to herbicides such as glyphosate, glufosinate, atrazine and imidazolidinone and to compounds having herbicidal activity such as sulfonylurea. In the typical embodiments, they have described some monocotyledonous weeds and dicotyledonous weeds that can be controlled by the synergistic herbicidal composition of the present invention, but they should not be considered as a limitation to certain species.

Examples of weed species that can be applied with the synergistic herbicidal composition of the present invention include monocotyledonous weeds, such as *Avena* spp., *Alopecurus* spp, *Apera* spp., *Brachiaria* spp., *Bromus* spp., *Digitaria* spp., *Lolium* spp., *Echinochloa* spp., *Leptochloa* spp., *Fimbristylis* spp., *Panicum* spp., *Phalaris* spp., *Poa* spp., *Setaria* spp.; and perennial variety include *Agropyron, Cynodon, Imperata* and *Sorghum* Moench.

As for dicotyledonous weeds, they include annual weed, such as *Abutilon* spp., *Amaranthus* spp., *Chenopodium* spp., *Chrysanthemum* spp., *Galium* spp., *Ipomoea* spp., *Kochia* spp., *Lamium* spp., *Matricaria* spp., *Pharbitis* spp., *Polygonum* spp., *Sida* spp., *Sinapis* spp., *Solanum* spp., *Stellaria* spp., *Veronica* spp., *Eclipta* spp., *Sesbania* spp., *Aeschynomene* spp. and *Viola* spp., *Xanthium* spp., and perennial variety, such as *Convolvulus, Cirsium, Rumex* and *Artemisia*.

Annual and perennial sedge weeds include *cyperus*, such as *Cyperus rotundus* L., *Cyperus esculentus* L., *Cyperus brevifolius* H., *Cyperus microiris* Steud, *Cyperus itria* L. and so on.

The herbicidal composition of the present invention has a broad herbicidal spectrum and preferably controls the following weeds: monocotyledonous weeds, for example *Echinochloa* spp., *Panicum* spp., *Poa* spp., *Leptochloa* spp., *Brachiaria* spp., *Digitaria* spp., *Setaria* spp., *cyperus, Monochoria* spp., *Fimbristylis* spp., *Sagittaria* spp., *Eleocharis* spp., *Scirpus* spp., *Alisma* spp., *Aneilema* spp., *Blyxa* spp., *Eriocaulon* spp., *Potamogeton* spp., particularly the following varieties: *Echinochloa oryzicola, Monochoria vaginalis, Eleocharis acicularis, Eleocharis kuroguwai, Cyperus difformis, Cyperus serotinus, Sagittaria pygmaea, Alisma canaliculatum, Scirpus juncoides*. For dicotyledonous weeds, the herbicidal spectrum has expanded to following groups: *Polygonum* spp., *Rorippa* spp., *Rotala* spp., *Lindernia* spp., *Bidens* spp., *Sphenoclea* spp., *Dopatrium* spp., *Eclipta* spp., *Elatine* spp., *Gratiola* spp., *Lindernia* spp., *Ludwigia* spp., *Oenanthe* spp., *Ranunculus* spp., *Deinostema* spp., and so on. Particularly includes following varieties: *Rotala indica, Sphenoclea zeylanica, Lindernia procumbens, Ludwigia prostrate, Potamogeton distinctus, Elatine triandra, Oenanthe javanica* and so on.

The present invention also relates to the use of the synergistic herbicidal composition in controlling the growth of undesirable plants within useful crops.

The herbicidal composition of the present invention is applicable for controlling/preventing the growth of undesirable plants in the useful crops (i.e., crops). Typically, the herbicidal composition of the present invention is applicable to control/prevent the growth of undesirable plants in the following crops:

Food crops, such as:

Cereal (small-sized grains), such as *Triticum aestivum*, and wheat crops, such as *T. durum, T. monococcum, T. dicoccon* and *T. spelta, Secale cereale, Tritiosecale, Hordeum vulgare;*

*Zea mays;*

Sorghum (such as *Sorghum bicolour*);

Rice (*Oryza*, such as *Oryza sativa* and *Oryza glaberrima*);

Sugarcane;

Beans (Legumes (Fabaceae)), such as *Glycine max.*, peanuts (*Arachis hypogaea*) and bean crops, such as green pea (including *Pisum sativum*, pigeon pea and cowpea), kidney bean (including *Vicia faba, Vigna* and *Phaseolus*) and hyacinth bean (*lens culinaris* var.);

Cruciferae, includes canola (*Brassica napus*), *Brassica napus, B. oleracea* var., *B. juncea, B. campestris, B. narinosa, B. nigra* and *B. tournefortii*; and *Brassica rapa* var.;

Other broadleaf crops, such as sunflower, cotton, flax, flaxseed, sugar beet, potato and tomato;

TNV crops (TNV: tree, nuts and cane), such as grapes, citrus, pome, such as apple and pear, coffee, pistachio and oil palm, stone fruits, such as peach, almond, walnut, olive, cherry, plum and apricot;

Turf, pasture and meadow;

Onion and garlic;

Ornamental bulbous plant, such as tulip and *narcissus;*

Conifer and deciduous tree, such as *pinus*, fir, oak, maple, *cornus*, hawthorn, crabapple and *rhamnus;*

Ornamental plants for garden, such as *Petunia hybrida*, marigold, rose and snapdragons.

The synergistic herbicidal composition of the present invention is particularly suitable for controlling/preventing the growth of undesirable plants among the useful crops, including wheat, barley, rye, triticale, durum wheat, rice, corn, sugarcane, sorghum, soybeans, peas, beans, lentils, peanuts, sunflower, sugar beet, potatoes, cotton, rapeseed, canola, mustard, cabbage, turnip, turf, grapes, apples, pears, stone fruit, peach, almond, walnut, olive, cherry, plum, apricot, citrus, coffee, pistachio, roses, petunias, marigolds, snapdragons, tulips, *narcissus*, fir, oak, maple, *cornus*, hawthorn and crabapple.

The synergistic herbicidal composition of the present invention is most suitable for controlling/preventing the growth of undesirable plants among the useful crops, including wheat, barley, rye, triticale, durum wheat, rice, corn, sugarcane, sorghum, soybeans, peas, beans and lentils, peanut, sunflower, sugar beet, potatoes, cotton, rapeseed, canola, mustard, cabbage, turnip, turf, grapes, peaches, almonds, walnuts, olives, cherry, plum, apricot, citrus and pistachio.

The present invention also provides a use of the synergistic herbicidal composition to control the growth of undesirable plants among the useful crops and the aforesaid synergistic herbicidal composition is resistant by the aforesaid useful crops.

The synergistic herbicidal composition of the present invention is also remarkably effective in control the growth of undesirable plants among non-crops areas, which includes road, railway, grassland, public pipeline and particularly undesirable plants growing in the areas covered with trees.

The synergistic herbicidal composition of the present invention is also applicable to following crop plants: which is resistant to one or more herbicides due to the genetic engineering or breeding, which is resistant to one or more pathogens, such as plant pathogenic fungi due to the genetic engineering or breeding, or which is resistant to insects attack due to genetic engineering or breeding. The suitable example is the crops which are resistant to synthesized growth hormone, preferably are corn, wheat, sunflower, rice, canola, oil rape, soy bean, cotton and sugarcane, or the crops which are resistant to the attack of certain insects as a result of introduction genes to Bt toxin by gene modification.

The synergistic herbicidal composition of the present invention can be applied through traditional skills known in the art. The suitable skills include spraying, atomizing, dusting, broadcast sawing or irrigation. The method of application can be determined by purpose; the skill should make sure the active components of the present invention can achieve optimum distribution under any circumstances.

The present invention also provides a method of controlling the growth of undesirable plants, comprising applying a herbicidal effective amount of synergistic herbicidal composition of the present invention to the undesirable plants or their locus of growth (i) before germination of the undesirable plant (pre-emergence); (ii) after germination of the undesirable plant (post-emergence), or (iii) (i) and (ii).

If the active components contained in the synergistic herbicidal composition of the present invention are applied on the surface of the soil before germination, then it can completely prevent the germination of weed seedling, or the weed will stop growing when it enters its cotyledon stage and then becomes dead two to four weeks thereafter.

If the aforesaid active components are applied to the green part of the plant after its germination, the growth of the weed will also stop immediately after the treatment, and the weed will remain in the stage when the herbicide is applied, or the weed is dead after a period of time. In this way, it can eliminate the competition from undesirable plants against useful crops earlier and sustainedly.

The present invention also provides a method of controlling the growth of undesirable plants, comprising applying the active ingredients of synergistic herbicidal composition of the present invention, namely Pyroxasulfone and Thifensulfuron methyl jointly or separately to the undesirable plants or their growing locus.

The aforesaid active compound may be applied to the undesirable plants (such as harmful plants, including monocotyledonous or dicotyledonous broadleaf weeds, gramineous weeds, sedge weeds or undesirable crop plants), seeds (such as caryopsis, seeds or vegetative propagation organ, including tuber or embryonic shoot) or growing locus (such as soil), preferably to apply at the green plants and parts of the plant, otherwise to apply to the soil if applicable.

The synergistic herbicidal composition of the present invention can comprise an effective amount of active components, namely Pyroxasulfone and Thifensulfuron methyl which has synergistic effects. The synergism can be observed when the active components Pyroxasulfone and Thifensulfuron methyl are applied jointly (for example used as combined formulation or tank mixture); the synergism can also be observed when the active compounds are applied at different time (separate application). The said herbicides or synergistic herbicidal composition can also be applied in portions (successive application), such as to apply at pre-emergence and then post-emergence, or it can also be applied after early emergence and then at medium or late stage of emergence. It is preferred to apply aforesaid active composition, namely Pyroxasulfone and Thifensulfuron methyl, jointly or almost simultaneously and particularly preferred to apply jointly. A possible use of the present invention is to apply said active compounds jointly in the form a tank-mixture, wherein the concentrate of optimum formulated active compounds is mixed with water in the tank and then apply the obtained spray solution.

There is synergistic effect when active components, namely Pyroxasulfone and Thifensulfuron methyl are applied jointly, that is, the activity of said synergistic herbicidal composition is higher than the anticipated activity of the sum of each herbicide. Synergism is able to reduce the application rate, control weeds with wider spectrum, including broadleaf weeds, gramineous weeds and sedge weeds, take effects more quickly, has longer effective duration and can better control the undesired plants and expand the application period by only one or several times of application to the undesirable plants. The effective dose of all active components in the said synergistic herbicidal composition, namely Pyroxasulfone and Thifensulfuron methyl can be adjusted to a relatively low level that reduce its effect to the soil to optimum degree. This character has enabled the composition to be applied to sensitive crops, and prevent groundwater pollution. The synergistic herbicidal composition of the present invention is able to reduce the application rate of active components significantly.

The present invention further provides a method of controlling the growth of undesirable plants, comprising applying the synergistic herbicidal composition of the present invention in the presence of plants, seeds or other reproductive parts of useful crops.

If the active components cannot be well resisted by some crops, then the herbicidal composition can be applied by the means of directive spraying with spraying equipment, in order to prevent touching the sensitive crops when they reach the leaves of undesirable plants growing beneath the crops or exposed soil.

The present invention also provides a method that can prevent or reduce the harms to the plants, seeds or other reproductive parts of useful crops after treatment of Pyroxasulfone, including the application of the synergistic herbicidal composition of the present invention to the plants, seeds or other reproductive parts of useful crops. The composition of Pyroxasulfone and Thifensulfuron methyl of the present invention has improved compatibility of Pyroxasulfone with agricultural crops.

The application rate of Pyroxasulfone can vary in a broad range, such as within 0.1 to 1000 g/ha, preferred 5 to 500 g/ha, still preferred 10 to 300 g/ha. Pyroxasulfone can control relatively wide spectrum of harmful plants when it is applied before sawing, at pre-planting or pre-emergence and post-emergence and the target plants include annual monocotyledonous or dicotyledonous broadleaf weeds, gramineous weeds and sedges, as well as any undesirable crop plants.

The application rate of Thifensulfuron methyl can vary in a wide range, such as within 1 to 500 g/ha, preferred 1 to 200 g/ha, more preferred 2 to 100 g/ha, particularly preferred 3 to 50 g/ha.

Normally, the application rate of the synergistic herbicidal composition of the present invention is low, such as within the range of 0.1 to 200 g/ha, preferred 0.5 to 100 g/ha, particularly preferred 1 to 50 g/ha, more preferred 1 to 30 g/ha.

FORMULATION EXAMPLES

Example 1: Suspension Concentrate of 60% Pyroxasulfone+6% Thifensulfuron Methyl

| | |
|---|---|
| Pyroxasulfone | 60% |
| Thifensulfuron methyl | 6% |
| triphenethyl phenol polyoxyethylene ether | 5% |
| p-methoxy fatty amide benzene sulfonate sodium | 5% |
| Bentonite | 1% |
| Glycerol | 5% |
| Urea | 5% |
| Water | Balance to 100% |

Suspension concentrate of 60% Pyroxasulfone+6% Thifensulfuron methyl is prepared by well mixing the active components, dispersant, wetting agent and water according to proportions of the formula through grinding and/or high speed shearing.

Example 2 Wettable Powder of 2% Pyroxasulfone+10% Thifensulfuron Methyl

| | |
|---|---|
| Pyroxasulfone | 2% |
| Thifensulfuron methyl | 10% |
| Polyoxyethylene glyceryl mono-fatty acid esters | 10% |
| Lauryl polyoxyethylene ether carboxylic acid sodium | 5% |
| Carbon white | 10% |
| Kaolin | Balance to 100% |

Wettable powder of 2% Pyroxasulfone+10% Thifensulfuron methyl is prepared by mixing active components, various adjuvants and fillers according to proportions of the formula and then milling the obtained mixture with superfine mill machine.

Example 3 Wettable Powder of 2% Pyroxasulfone+50% Thifensulfuron Methyl

| | |
|---|---|
| Pyroxasulfone | 2% |
| Thifensulfuron methyl | 50% |
| Fatty alcohol polyoxyethylene ether | 1% |
| Alkylphenol polyoxyethylene ether formaldehyde condensate | 2% |
| Carbon white | Balance to 100% |

Wettable powder of 2% Pyroxasulfone+50% Thifensulfuron methyl is prepared by mixing active components, various adjuvants and fillers according to proportions of the formula, and then milling the obtained mixture with superfine mill machine.

Example 4 Water-Dispersible Granule of 5% Pyroxasulfone+50% Thifensulfuron Methyl

| | |
|---|---|
| Pyroxasulfone | 5% |
| Thifensulfuron methyl | 50% |
| Sodium Salts of Naphthalene Sulfonated Formaldehyde condensate | 4% |
| Sodium Dodecyl Sulfate | 5% |
| Urea | 5% |
| Kaolin | Balance to 100% |

Water-dispersible granule of 5% Pyroxasulfone+50% Thifensulfuron methyl is prepared by well mixing the active components, dispersant, wetting agent, disintegrating agent and filler according to proportions of the formula, and then milling the obtained mixture through jet milling, then adding some water to extrude paste which is dried and sieved in the end.

Example 5 Emulstifiable Concentrate of 0.5% Pyroxasulfone+50% Thifensulfuron Methyl

| | |
|---|---|
| Pyroxasulfone | 0.5% |
| Thifensulfuron methyl | 50% |
| ethoxylated castor oil | 5% |
| Calcium dodecylbenzene sulfonate | 3% |
| SOLVESSO™ 100 | Balance to 100% |

The above components are prepared according to the proportions and then well stirred to obtain homogeneous phase.

Example 6 Aqueous Suspo-Emulsion of 0.5% Pyroxasulfone+25% Thifensulfuron Methyl

| | |
|---|---|
| Pyroxasulfone | 0.5% |
| Thifensulfuron methyl | 25% |
| Sodium methyl naphthalene sulfonate formaldehyde condensates | 5% |
| ethoxylated caster oil | 3% |
| bentonite | 1% |
| SOLVESSO™ 100 | 20% |
| Urea | 5% |
| Water | Balance to 100% |

Aqueous suspo-emulsion of 0.5% Pyroxasulfone+25% Thifensulfuron methyl is prepared by following steps: the suspension concentrate of Thifensulfuron methyl is obtained by grinding and/or high speed shearing of Thifensulfuron methyl, Sodium methyl naphthalene sulfonate formaldehyde condensates and water; the emulstifiable concentrate of Pyroxasulfone is obtained by well stirring the mixture of Pyroxasulfone, SOLVESSO™ 100 and ethoxylated caster oil; in the end, the emulstifiable concentrate of Pyroxasulfone is added to the suspension concentrate of Thifensulfuron methyl to obtain above aqueous suspo-emulsion.

Example 7 Wettable Powder of 10%, Pyroxasulfone+50% Thifensulfuron Methyl

| | |
|---|---|
| Pyroxasulfone | 10% |
| Thifensulfuron methyl | 50% |
| Alkylphenol polyoxyethylene ether phosphate | 10% |
| Nonylphenol polyoxyethylene ether | 5% |
| Carbon white | 10% |
| Kaolin | Balance to 100% |

The wettable powder is prepared by mixing the above components according to the proportions, and then grinding and crushing the obtained mixture.

Example 8 Water-Dispersible Granule of 5% Pyroxasulfone+50% Thifensulfuron Methyl

| | |
|---|---|
| Pyroxasulfone | 5% |
| Thifensulfuron methyl | 50% |
| Sodium naphthalene sulfonate formaldehyde condensates | 5% |
| Sodium dodecyl sulfate | 5% |
| Urea | 5% |
| Kaolin | Balance to 100% |

Water-dispersible granule of 5% Pyroxasulfone+50% Thifensulfuron methyl is prepared by following steps: well-mix the active components, namely Pyroxasulfone and Thifensulfuron methyl, dispersant, wetting agent, disintegrating agent and filler according to proportions of the formula and then prepare the wettable powder by jet milling the obtained mixture; then add some water to extrude paste which is dried and sieved in the end.

Example 9 Oil-in-Water Emulsion of 1% Pyroxasulfone+10% Thifensulfuron Methyl

| | |
|---|---|
| Pyroxasulfone | 1% |
| Thifensulfuron methyl | 10% |
| SOLVESSO™200 | 10% |
| Ethoxylated caster oil | 5% |
| SOPROPHOR®4D384(from RHODIA) | 1% |
| Water | Balance to 100% |

Dissolve the Pyroxasulfone and Thifensulfuron methyl into SOLVESSO™200 and add ethoxylated caster oil to obtain oil phase; well mix the SOPROPHOR®4D384 and water according to formula to obtain aqueous phase; add the oil phase into the aqueous phase with stirring to obtain oil-in-water emulsion.

Example 10 Wettable Powder of 50% Pyroxasulfone+5% Thifensulfuron Methyl

| | |
|---|---|
| Pyroxasulfone | 50% |
| Thifensulfuron methyl | 5% |
| Polyoxyethylene glyceryl mono-fatty acid esters | 5% |
| Polyoxyethylene lauryl ether carboxylic acid sodium | 5% |
| Highly dispersed silicon acid | 1% |
| Kaolin | Balance to 100% |

The wettable powder is prepared by mixing the above components according to the proportions and grinding, crushing the obtained mixture.

Example 11 Coated Granule of 50%° Pyroxasulfone+1% Thifensulfuron Methyl

| | |
|---|---|
| Pyroxasulfone | 50% |
| Thifensulfuron methyl | 1% |
| Polyethylene glycol | 3% |
| Carboxyethyl cellulose | 6% |
| Calcium carbonate | Balance to 100% |

In the mixer, the carrier wetted by polyethylene glycol is evenly coated with grinded active components. The dust-free coated granules can be obtained through this manner.

Example 12 Wettable Powder of 50% Pyroxasulfone+2% Thifensulfuron Methyl

| | |
|---|---|
| Pyroxasulfone | 50% |
| Thifensulfuron methyl | 2% |
| p-methoxy fatty amide benzene sulfonate sodium | 3% |
| triphenethyl phenol polyoxyethylene ether | 2% |
| Kaolin | Balance to 100% |

The wettable powder is prepared by mixing the above components according to the proportions and grinding, crushing the obtained mixture.

Example 13 Extruded Granule of 25% Pyroxasulfone+5% Thifensulfuron Methyl

| | |
|---|---|
| Pyroxasulfone | 25% |
| Thifensulfuron methyl | 5% |
| p-methoxy fatty amide benzene sulfonate sodium | 4% |
| Carboxymethyl cellulose | 2% |
| Kaolin | Balance to 100% |

Mix and grind the active components and adjuvant, and use water to wet the mixture. Extrude the mixture which is dried in the air flow.

Example 14 Seed Coating Agent of 0.5% Pyroxasulfone+5% Thifensulfuron Methyl

| | |
|---|---|
| Pyroxasulfone | 0.5% |
| Thifensulfuron methyl | 5% |
| Sorbitan Monostearate | 10% |
| Alkyl dimethyl benzyl ammonium salt | 5% |
| Aluminum magnesium silicate | 1% |
| Bentonite | 1% |
| Glycerol | 5% |
| PVP-K30 | 1% |
| Water | Balance to 100% |

The seed coating agent is prepared by well-mixing above components according to the proportions and sand milling.

Example 15 Microencapsulated Suspension of 5% Pyroxasulfone+5% Thifensulfuron Methyl

| | |
|---|---|
| ATLOX™4913 | 2% |
| Citric acid | 0.05% |
| Triethylenetetramine | 0.5% |
| Water | 13% |
| Thifensulfuron methyl | 5% |
| PAPI | 1.35% |
| SOLVESSO™100 | 10% |
| ATLOX™4913 | 16% |
| triphenethyl phenol polyoxyethylene ether | 0.3% |
| Silicone | 0.16% |
| Urea | 4% |
| Pyroxasulfone | 5% |
| Water | Balance to 100% |

Add the oil phrase consisting of PAPI (polymethylene polyphenyl polyisocyanate), Thifensulfuron methyl and SOLVESSO™ 100 into aqueous solution containing ATLOX™4913 to form emulsion. Then heat the obtained product and keep warm at 50° C. when add catalyst to react for 2 hrs. The microcapsules of Thifensulfuron methyl are obtained after cooling.

Well-mix ATLOX™4913, triphenethyl phenol polyoxyethylene ether, silicon, urea, Pyroxasulfone and water according to the proportions and sand milling the obtained mixture to prepare suspension.

Add the obtained microcapsules of Thifensulfuron methyl into the suspension of Pyroxasulfone, then well stir obtained product to prepare Microencapsulated suspension of 5% Pyroxasulfone+5% Thifensulfuron methyl.

Example 16 Aqueous Suspo-Emulsion of 5% Pyroxasulfone+20% Thifensulfuron Methyl

| | |
|---|---|
| Pyroxasulfone | 5% |
| Thifensulfuron methyl | 20% |
| SOLVESSO™ 200 | 10% |
| Ethoxylated castor oil | 4% |
| Fatty alcohol polyoxyethylene ether sulfosuccinate monoester disodium | 5% |
| Modified lignosulphonate calcium | 5% |
| Xanthan gum | 1% |
| Bentonite | 1% |
| Glycerol | 5% |
| Water | Balance to 100% |

Dissolve Thifensulfuron methyl into SOLVESSO™ 200 and add ethoxylated castor oil to obtain Thifensulfuron methyl EC;

The suspension concentrate is prepared by well-mixing Pyroxasulfone, Fatty alcohol polyoxyethylene ether sulfosuccinate monoester disodium and modified lignosulphonate calcium according to the proportions and sand milling the obtained mixture.

The suspo-emulsion is prepared by adding the oil phase of Thifensulfuron methyl into suspension concentrate comprising Pyroxasulfone.

Example 17 Emulstifiable Concentrate of 5% Pyroxasulfone+5% Thifensulfuron Methyl

| | |
|---|---|
| Pyroxasulfone | 5% |
| Thifensulfuron methyl | 5% |
| Ethoxylated castor oil | 5% |
| Calcium dodecylbenzene sulfonate | 3% |
| SOLVESSO™ 200 | Balance to 100% |

Mix the above components and well stir to obtain transparent homogeneous phase.

Example 19 50% Pyroxasulfone+50% Thifensulfuron Methyl

| | |
|---|---|
| Pyroxasulfone | 50% |
| Thifensulfuron methyl | 50% |

Well-mix the Pyroxasulfone and Thifensulfuron methyl according to the proportions.

Example 20 30% Pyroxasulfone+30% Thifensulfuron Methyl+40% Isoxadifen-Ethyl

| | |
|---|---|
| Pyroxasulfone | 30% |
| Thifensulfuron methyl | 30% |
| Isoxadifen-ethyl | 60% |

Well-mix Pyroxasulfone, Thifensulfuron methyl and Isoxadifen-ethyl according to the proportions.

Example 21 60% Pyroxasulfone+40% Thifensulfuron Methyl

| | |
|---|---|
| Pyroxasulfone | 60% |
| Thifensulfuron methyl | 40% |

Well-mix Pyroxasulfone and Thifensulfuron methyl according to the proportions.

Example 22 15% Pyroxasulfone+50% Thifensulfuron Methyl+35% Fenclorim

| | |
|---|---|
| Pyroxasulfone | 15% |
| Thifensulfuron methyl | 50% |
| Fenclorim | 35% |

Well-mix Pyroxasulfone, Thifensulfuron methyl and Fenclorim according to the proportions.

Biology Test Example

The assessment on the synergistic effect of mixing two or more herbicidal active ingredients is determined based on the Colby's equation as described in "Calculation Synergistic and Antagonistic Response of Herbicide Combinations (Weeds 15/1 (1967), S. R. Colby)".

The calculation formula (1) is set out below:

$$E_0 = X + Y - \frac{XY}{100} \tag{1}$$

Wherein Formula (1), X represents weeds control percentage (%) of herbicides A at the dosage of Xg effective ingredients per ha; Y represents weeds control percentage (%) of herbicides B at the application rate of Yg effective ingredients per ha; represents the expected weeds control percentage (%) at the application rate of X+Yg active ingredients per ha.

If the actual efficiency of weed control percentage observed during biology test exceeds the expected value ($E_0$) as calculated via Colby's equation, then it represents that the efficacy of herbicidal composition is greater than the sum of efficacy of each component, which means the composition has synergistic effect.

Pre-Emergence Test:

Under greenhouse, place the seeds or the root tubers of monocotyledonous weeds and dicotyledonous weeds in a pot containing sandy clay and cover it with soil. Use standard soil as growing media. At pre-emergence stage, apply the herbicides separately or in the form of mixture on the surface of the soil. After the treatment, put the pot in greenhouse and keep it under the condition suitable for the growth of weeds. By comparing with untreated control group, conduct the visual assessment on the plant damage after 3 to 4 weeks of test circle or on the plant damage after emergence. As shown in the test results, the application of synergistic herbicidal composition of embodiments of the present invention has excellent herbicidal activity to wide-spectrum of weeds at pre-emergence stage. The observation data from the test has indicated that the activity of synergistic herbicidal composition of embodiments of the present invention has exceeded the anticipated value as calculated through Colby formula when applied at a suitable low-level of application rate, presenting significant synergistic effect.

Post-Emergence Test:

Use stem and leaf treatment for potted grown plant (NY/T 1155.4-2006): fill a plastic pot (6 cm height, 9 cm diameter) with a quantity of soil and sow 15 to 20 seeds of monocotyledonous weeds and dicotyledonous weeds in the plastic pot, cover it with 0.5 to 1 cm thick of fine soil and then put it in greenhouse for cultivation. When weeds grow to the 2 to 4 leave stage, conduct the stem and leaf spray treatment with 1 mL herbicidal solution on each pot and repeat four times for each treatment and leave some pots untreated as control group. Keep the treated pots in a greenhouse for cultivation and observe the growing status of target weeds periodically. Conduct the visual test on the target weeds regarding the damage symptoms and growth inhibition effect after 21 days. Weigh up the fresh weight above the ground or plant fresh weight and evaluate the toxicity of the herbicidal formulation on target weeds based on the fresh weight inhibition rate of the target.

Prepare the following three formulations according to specific weight percentages: 1. Pyroxasulfone; 2. Thifensulfuron methyl; 3 Pyroxasulfone+Thifensulfuron methyl. After that, dilute above formulations with water to obtain diluted formulations.

Investigation Method:

Conduct visual assessment the damage symptom and growth inhibition status of target weeds after 21 days. Weigh up the fresh weight above the ground and calculate the inhibition rate of fresh weight (%).

$$FreshWeightInhibitionRate\ P\ (\%) = \frac{Fresh weight of control group - Fresh weight of treated group}{Fresh weight of control group} \times 100$$

The assessment on the synergistic effect of mixing two or more herbicidal active ingredients is determined based on the Colby's equation as described in "Calculation Synergistic and Antagonistic Response of Herbicide Combinations (Weeds 15/1(1967), S. R. Colby)".

$$E_0 = X + Y - \frac{X \times Y}{100}$$

Wherein, X represents Fresh Weight Inhibition Rate of Pyroxasulfone when applied alone at certain application rate against target weeds;

Y represents the Fresh Weight Inhibition Rate against target weeds when Thifensulfuron methyl is applied alone at certain application rate;

$E_0$ represents the theoretical value of Fresh Weight Inhibition Rate against target weeds when applying the mixture of Pyroxasulfone and Thifensulfuron methyl;

E represents the measured value of Fresh Weight Inhibition Rate against target weeds when applying the mixture of Pyroxasulfone and Thifensulfuron methyl.

If the actual efficiency (E) of weed control percentage observed during biology test exceeds the expected value ($E_0$) as calculated via Colby's equation, then it represents that the efficacy of herbicidal composition is greater than the sum of efficacy of each component, which means the composition has synergistic effect.

The synergistic herbicidal composition of embodiments of the present invention has been tested on the following important harmful plants (gramineous weeds, broadleaf weeds, sedge weeds) with wide herbicidal spectrum: *Echinochloa oryzicola*, *Digitaria* spp., *Stellaria media*, *Amaranthus retroflexus*, *Fallopia* (ex *Polygonum*)*Convolvulus*, *Abuthilon theophrasti*, *Sagittariatrifolia*, Oriental Waterplantain Rhizome, Herb of Pygmy Arrowhead, *Monochoria korsakowii*, *Lindernia procumbens*, *Solanum nigrum* L., *Scirpus juncoides* Roxb, *Cyperus difformis* L., *Chenopodium alum* L., *Avena fatua* L. and *Galium aparine* L. var. *tenerum* Gren. et (Godr.) Rebb.

| | | Herbicidal Activity % | |
|---|---|---|---|
| Pyroxasulfone | Thifensulfuron methyl | Experimental | Predictive |
| Application Rate by g ai/ha | | Data | Value |
| 1 | 0 | 11 | — |
| 5 | 0 | 22 | — |
| 10 | 0 | 40 | — |
| 25 | 0 | 49 | — |
| 50 | 0 | 63 | — |
| 0 | 1 | 0 | |
| 0 | 5 | 15.5 | |
| 0 | 10 | 31.2 | — |
| 0 | 25 | 55.1 | — |
| 0 | 50 | 60.3 | — |
| 50 | 1 | 68.1 | 63.00 |
| 25 | 1 | 58.3 | 49.00 |
| 10 | 1 | 49.9 | 40.00 |
| 5 | 1 | 34.9 | 22.00 |
| 5 | 5 | 47.8 | 34.09 |
| 1 | 5 | 37.8 | 24.80 |
| 1 | 10 | 49.5 | 38.77 |
| 1 | 25 | 68.5 | 60.04 |
| 1 | 50 | 74.2 | 64.67 |

The test result shows that when applying the composition of Pyroxasulfone and Thifensulfuron methyl with the range of 50:1 to 1:50, it represents obvious synergistic effect in controlling gramineous weeds, broadleaf weeds and sedge weeds.

The weed control efficacy of the synergistic herbicidal composition of embodiments of the present invention is superior to the efficacy of each component being applied separately. The pesticide effect test has demonstrated that the composition has synergistic effect and has the characteristics of expanded herbicidal spectrum, controlling gramineous weeds, broadleaf weeds and sedge weeds in the field by a single application, reducing times of application, decreasing control cost, delaying the occurrence of weed resistance, safe to crops and consistent with safety requirements for pesticides. It is applicable to corn, soybean, cereal, sunflower, potato, peanut, cotton with fief weeding at pre-emergence or weeding at post-emergence.

Safety Effect:

Under greenhouse, sow the seeds of wheat for testing in a plastic tank till they grow to 4 leaf stage. During the stage, apply the Pyroxasulfone, Thifensulfuron methyl and the composition of Pyroxasulfone+Thifensulfuron methyl on the testing plants. Evaluate the phytotoxicity of the herbicides against crops measured by percentage. 100% represents the testing plants completely die, while 0% represents no phytotoxicity exist.

| Pyroxasulfone Application Rate by g ai/ha | Thifensulfuron methyl | Phytotoxicity % Experimental Data |
| --- | --- | --- |
| 1 | 0 | 0 |
| 5 | 0 | 0 |
| 10 | 0 | 11 |
| 25 | 0 | 13 |
| 50 | 0 | 17 |
| 0 | 1 | 0 |
| 0 | 5 | 0 |
| 0 | 10 | 0 |
| 0 | 25 | 0 |
| 0 | 50 | 0 |
| 50 | 1 | 0 |
| 25 | 1 | 0 |
| 10 | 1 | 0 |
| 10 | 5 | 0 |
| 25 | 5 | 0 |
| 50 | 5 | 0 |
| 10 | 10 | 0 |
| 25 | 10 | 0 |
| 50 | 10 | 0 |
| 10 | 25 | 0 |
| 25 | 25 | 0 |
| 50 | 25 | 0 |
| 10 | 50 | 0 |
| 25 | 50 | 0 |
| 50 | 50 | 0 |

It can be observed that the combination of Pyroxasulfone and Thifensulfuron methyl has improved the compatibility of Pyroxasulfone to crops and reduced or prevented harms to the plants, seeds or other reproductive parts of useful crops which have been treated by Pyroxasulfone.

Throughout the specification and the claims that follow, unless the context requires otherwise, the words "comprise" and "include" and variations such as "comprising" and "including" will be understood to imply the inclusion of a stated integer or group of integers, but not the exclusion of any other integer or group of integers.

The reference to any prior art in this specification is not, and should not be taken as, an acknowledgement of any form of suggestion that such prior art forms part of the common general knowledge.

It will be appreciated by those skilled in the art that the invention is not restricted in its use to the particular application described. Neither is the present invention restricted in its preferred embodiment with regard to the particular elements and/or features described or depicted herein. It will be appreciated that the invention is not limited to the embodiment or embodiments disclosed, but is capable of numerous rearrangements, modifications and substitutions without departing from the scope of the invention.

The invention claimed is:

1. A herbicidal composition comprising a synergistically effective amount of Pyroxasulfone and Thifensulfuron methyl as the active components, wherein the weight ratio of Pyroxasulfone and Thifensulfuron methyl ranges from 5:1 to 1:5.

2. The herbicidal composition of claim 1, further comprising a surfactant and/or filler.

3. The herbicidal composition of claim 2, wherein said active components of Pyroxasulfone and Thifensulfuron methyl is present in the herbicidal composition in an amount of 5% to 90% by weight, based on the total weight of the composition.

4. The herbicidal composition of claim 2, wherein said active components of Pyroxasulfone and Thifensulfuron methyl is present in the herbicidal composition in an amount of 10% to 80% by weight, based on the total weight of the composition.

5. The herbicidal composition of claim 2, wherein said active components of Pyroxasulfone and Thifensulfuron methyl is present in the herbicidal composition in an amount of 20% to 60% by weight, based on the total weight of the composition.

6. The herbicidal composition of claim 1, wherein the composition is provided as a formulation selected from a wettable powder (WP), an emulsifiable concentrate (EC), a suspension concentrate (SC), a capsule suspension (CS), a micro-emulsion (ME), an oil-in-water emulsion (EW), suspoemulsion (SE), water dispersible granules (WDG), an aqueous solution (AS), a capsule suspension (CS) and an ultra-low volume liquid (ULV).

7. A method of controlling the growth of undesirable plants comprising applying the herbicidal composition of claim 1 to the undesirable plants or their growing locus.

8. A method of eliminating the growth of undesirable plants comprising applying the herbicidal composition of claim 1 to the undesirable plants or their growing locus.

9. The method of claim 7, wherein the undesirable plants are selected from broadleaf weeds, sedge weeds and gramineous weeds.

10. A method of controlling the growth of undesirable plants, comprising applying a herbicidal effective amount of the herbicidal composition of claim 1 to the undesirable plants or their growing locus (i) before germination of the undesirable plant (pre-emergence); (ii) after germination of the undesirable plant (post-emergence), or (iii) (i) and (ii).

11. A method of controlling the growth of undesirable plants, comprising applying the active components Pyroxasulfone and Thifensulfuron methyl of the herbicidal composition of claim 1 to the undesirable plants or their growing locus jointly or separately.

12. A method to control the growth of undesirable plants, comprising applying the herbicidal composition of claim 1 in the presence of plants, seeds or other reproductive parts of useful crops.

13. A method of reducing or preventing harm from Pyroxasulfone when applied to plants, seeds or other reproductive parts of useful crops, comprising applying Pyroxasulfone in the herbicidal composition according to claim 1 on the plants, seeds or other reproductive parts of the useful crops.

* * * * *